US00PP33266P2

(12) United States Plant Patent
Hansen

(10) Patent No.: US PP33,266 P2
(45) Date of Patent: Jul. 13, 2021

(54) ***HOSTA* PLANT NAMED 'HOPE SPRINGS ETERNAL'**

(50) Latin Name: ***Hosta* hybrid**
Varietal Denomination: Hope Springs Eternal

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,300

(22) Filed: Dec. 18, 2020

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12; A01H 5/02
See application file for complete search history.

*Primary Examiner* — Keith O. Robinson

(57) ABSTRACT

A new and distinct *Hosta* plant named 'Hope Springs Eternal' with medium, rounded-mound habit of heavy-substance, stiff, variegated foliage. Leaves are glaucous, broadly ovate with undulate margins, creamy-white margins, bluish-green centers and intermediate colors between. Flowers have pale purple margins with slightly darker veins, held above foliage beginning in early July. The new plant is attractive for landscaping in the garden as a specimen, in mass and as a container.

2 Drawing Sheets

Latin name and variety denomination of the plant:
Botanical classification: *Hosta* hybrid.
Variety denomination: 'Hope Springs Eternal'.

STATEMENT REGARDING PRIOR DISCLOSURES UNDER 37 CFR 1.77(B)(6)

*Hosta* 'Hope Springs Eternal' was first introduced by the inventor as a non-enabling description through the International Cultivar Registration Authority registration in early 2020. No plants of *Hosta* 'Hope Springs Eternal' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Hope Springs Eternal' hereinafter also referred to as the new plant or just the cultivar name, 'Hope Springs Eternal'. *Hosta* 'Hope Springs Eternal' was single seedling selection from a cross in the summer of 2011 by the inventor at a wholesale perennial nursery in Zeeland, Mich., USA between the non-patented, unreleased, proprietary hybrid known only as 'H9-310' as the female parent and the non-patented, unreleased, proprietary hybrid known only as 'H9-57' as the male parent. The new plant was assigned the breeder code 11-397-18 and passed the initial evaluation in the summer of 2015. The new plant has been asexually propagated by division at the same nursery in Zeeland, Mich., USA since 2017 and also by careful plant shoot-tip tissue culture with the resultant asexually propagated plants having retained all the same traits as the original plant.

BRIEF SUMMARY OF THE PLANT

There are over 7,000 registered and unregistered *Hosta* cultivars recognized by The American *Hosta* Society, which is the International Cultivar Registration Authority for the genus *Hosta*. The nearest known comparison cultivars are *Hosta* 'Chantilly Lace' (not patented), 'El Nino' (not patented), 'Autumn Frost' U.S. Plant Pat. No. 23,224, 'Blue Ivory' U.S. Plant Pat. No. 19,623, 'Hunters Ridge' (not patented), 'Sleeping Beauty' (not patented), 'Wolverine' (not patented) and 'Voices in the Wind' copending U.S. Plant Patent Application.

All of the above plants have a green to bluish-green center and a lighter variegated margin. 'Chantilly Lace' has a smaller habit with smaller narrower leaves that are less bluish and less marginal undulation. 'El Nino' and 'Sleeping Beauty' both have foliage that lacks the undulation in the margins. 'Autumn Frost' has a similar habit and leaf shape, but the margin is more yellow and the foliage lacks the undulation. 'Blue Ivory' has a wider margin without the undulation, but the habit is similar. 'Hunters Ridge' has a smaller habit with smaller foliage that are less bluish with more veins and flowering season is later. 'Wolverine' has a narrower leaf that is slightly less bluish-green and lacks the marginal undulation. 'Sleeping Beauty' has a smaller habit, smaller lanceolate foliage with narrower margins without undulations. 'Voices in the Wind' has smaller habit with longer more arching foliage that has a more yellowish margin that is more undulated.

The female parent has leaves that are irregularly streaked creamy white and deep green in a mericlinal chimera pattern and has a larger habit with larger and more elongated leaves and the flowers are lighter lavender compared to the new plant. The male parent has narrower, more bluish leaves without variegation.

Other *Hosta* cultivars have similar colored variegated foliage, but 'Hope Springs Eternal' is distinct from the above listed *Hostas* and all other cultivars known to the inventor by the following combined traits:

1. Medium-sized, round-mounded plant habit with heavy-substance, stiff, variegated foliage;
2. Glaucous leaves are broadly ovate with intense rippling along the margins;
3. Leaf margins are creamy-white and centers are bluish-green with intermediate colors between;
4. Medium-sized flowers are on strongly upwardly projecting scapes above foliage;
5. Tepals are medium lavender with slightly darker veins and clear margins.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
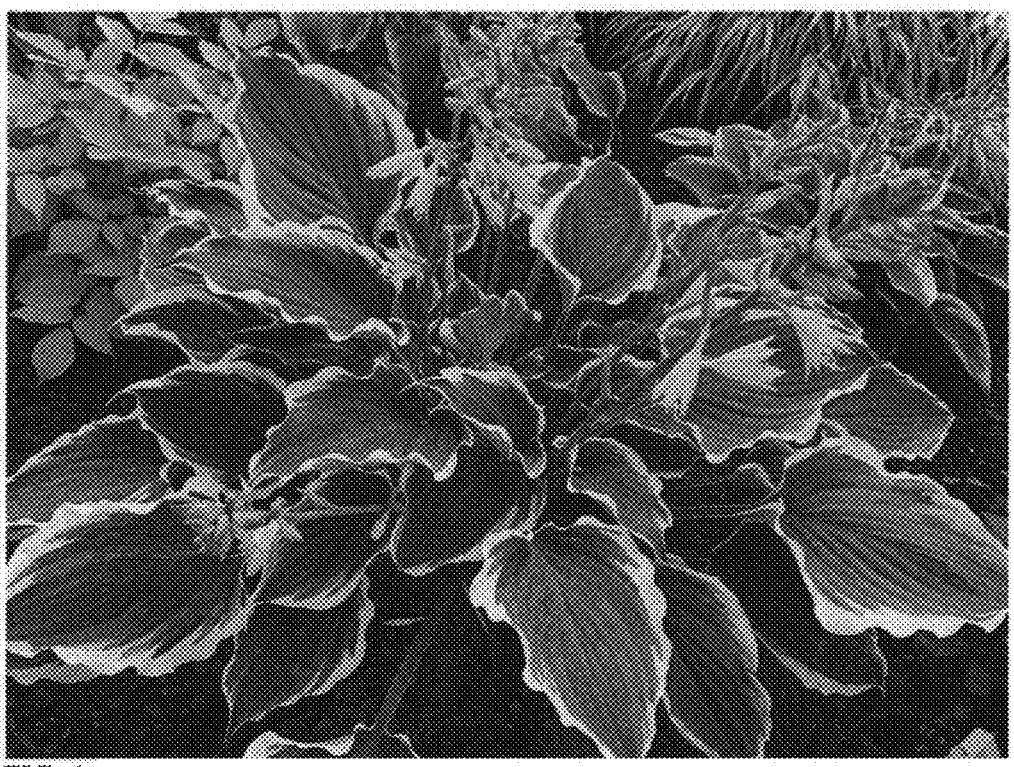
FIG. 1 shows the habit of a five-year-old plant with early flowers and buds.
Figure 2:
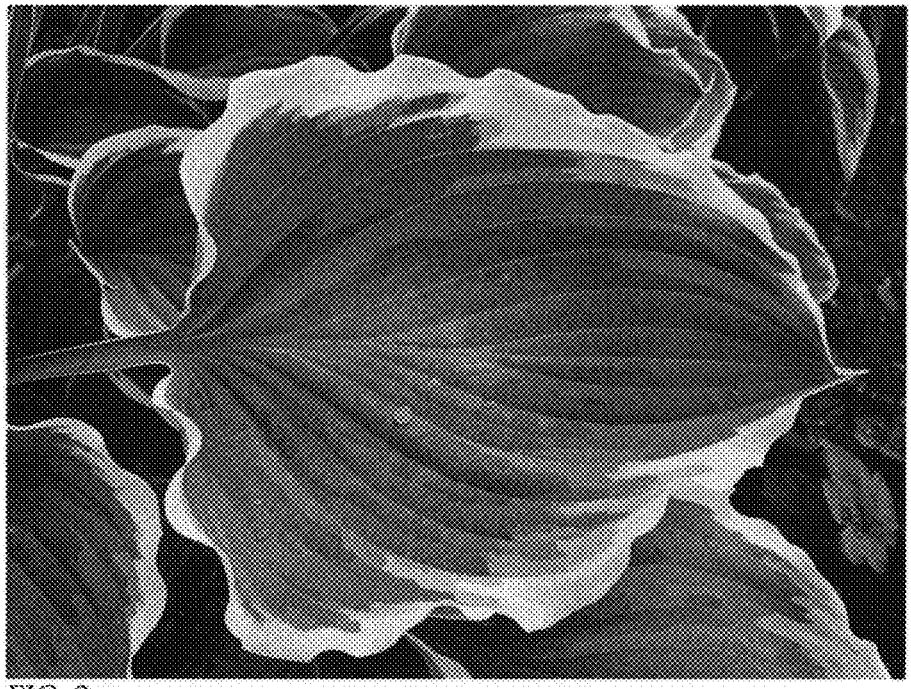
FIG. 2 shows a close-up of the foliage with variegation.
Figure 3:
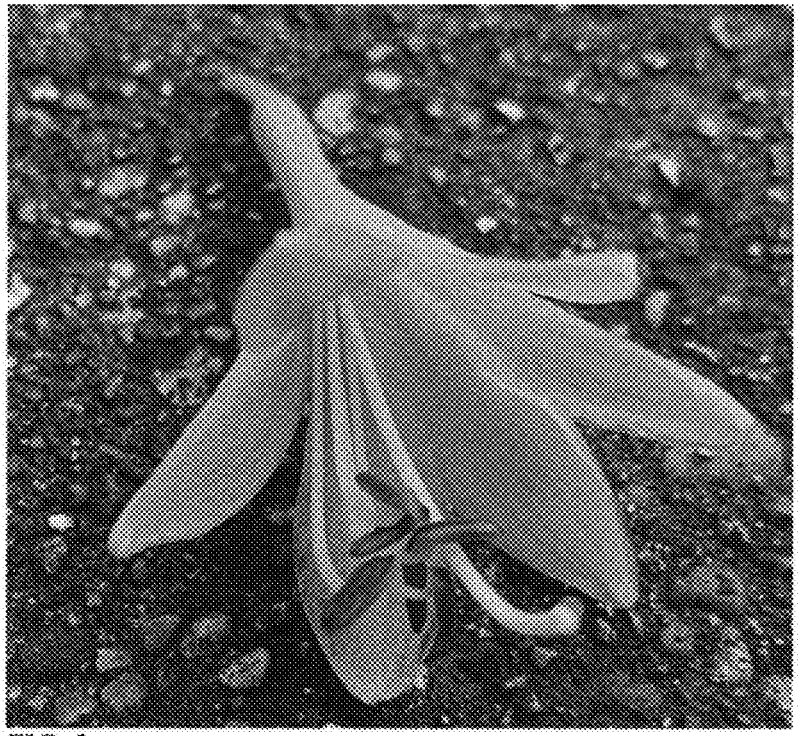
FIG. 3 shows a close-up of a flower.

The following descriptions and color references are based on the 2015 edition of The Royal Horticultural Society Colour Chart except where common dictionary terms are used. The new plant, *Hosta* 'Hope Springs Eternal', has not been observed under all possible environments. The phenotype may vary slightly with different environmental conditions, such as temperature, light, fertility, moisture and maturity levels, but without any change in the genotype. The following observations and size descriptions are of a seven-year old plant in a partially shaded trial garden in Zeeland, Mich. with supplemental water and fertilizer.

Botanical classification: *Hosta* hybrid;

Parentage: 'H9-310' as the female parent and 'H957' as the male parent which have in their background 'Niagara Falls' (not patented), 'Fulda' (not patented), 'Neptune' U.S. Plant Pat. No. 19, 674 and a proprietary, unnamed selection of *H. rupifraga* (not patented);

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155A and RHS NN155B;

Plant shape and habit: Hardy herbaceous perennial with basal rosettes of leaves emerging from rhizomes producing a large, symmetrical, rounded-mound of leaves; about 12 divisions per plant; divisions to about 3.0 cm diameter at soil level;

Plant size: Foliage height about 56.0 cm above soil line to the top of the leaves and about 119.4 cm wide at the widest point about 20 cm above the soil line;

Foliage description: Broadly ovate; acute apex; cordate base; entire undulate margin; glabrous and highly glaucous adaxial, and glabrous and moderately glaucous abaxial; blades mostly flat in center with margin undulate; with a thick stiff feel;

Leaf blade size: To about 26.7 cm long, 20.3 cm wide at base; average about 24.0 cm long and 18.5 cm wide; with variegated margin of variable width between 1.3 cm and 5.1 cm wide;

Leaf blade color: Early season and expanding margin adaxial nearest RHS 11B, adaxial center nearest RHS 137B with intermediate colors comprising nearest RHS N144A, between RHS 146D and between RHS 148D and RHS 145C, abaxial margin nearest RHS 4D and abaxial center between RHS 138B and RHS 138A with intermediate colors comprising RHS 145B and between RHS 145C and RHS 148D; mid-season and later summer adaxial margin between RHS 155B and NN155B, center nearest RHS 137B with loss of wax late in season, and prior to losing wax between RHS N138A and RHS 122A, intermediate region variable comprising RHS 148C, between RHS 145C and RHS 146D, RHS N138D and RHS 148D; mid-season and later abaxial margin between RHS 155B and RHS NN155B, center between RHS 155B and RHS NN155B and intermediate comprising a blend between RHS 145C and 148D, RHS 145C and RHS 145B;

Petiole: Entire, glabrous, deeply concavo-convex; stiff; mostly straight from base of plant to leaf base with little bending or arching, strong and slightly flexible; to about 28.5 cm long and 9.0 mm wide at base and 6 mm deep;

Petiole color: Adaxial margin about 2.5 mm wide nearest RHS 158C, center nearest RHS 137B; abaxial margin nearest RHS 146B with a thin 1.0 mm proximal portion nearest RHS 158A, center nearest RHS 146D;

Veins: Parallel, lightly impressed adaxial, moderately bulging, costate abaxial side; about 10 to 11 pairs and one main center vein;

Veins color: Adaxial same as surrounding tissue; abaxial midrib proximally nearest RHS 146D, distal midrib and marginal veins same as surrounding tissue;

Flower description: Perfect; single; actinomorphic; funnel-form; held outwardly to slightly drooping; persist for normal period, usually one day on plant or as cut flower; about 36 flowers per scape;

Flower period: Scapes remain effective with flowering beginning early July for about three weeks in Michigan;

Flower size: About 52.0 mm long to exserted style; corolla to about 44.0 mm long and flared to about 45.0 mm across; corolla tube to about 22.0 mm long and 5.0 mm diameter toward base;

Fragrance: None detected;

Floral bracts: Subtending individual flowers; lanceolate to linear; narrowly acute apex, truncate clasping base, margin entire; glabrous adaxial and abaxial; to about 55.0 mm long and 10.0 mm across, decreasing in size distally;

Bract color: Adaxial margin nearest RHS 158D, center nearest RHS 146C; abaxial margin RHS 158D, center nearest RHS 147C and moderate blush proximally nearest RHS N77C;

Tepals: Two sets of three; lanceolate with acute apex and fused base;

*Inner set.*—56.0 mm long and 11.0 mm across slightly above fusion; fused in basal 24.0 mm and free in distal 22.0 mm; vitreous along 1.0 mm wide margin.

*Inner set color.*—Adaxial nearest RHS 91C with veins nearest RHS 91B and corolla tube lighter than RHS 91D; abaxial including corolla tube nearest RHS 91D.

*Outer tepal.*—56.0 mm long and 10.0 mm across slightly above fusion; fused in basal 24.0 mm and free in distal 22.0 mm; not vitreous along margin.

*Outer tepal color.*—Adaxial nearest RHS 91C with veins nearest RHS 91B and corolla tube lighter than RHS 91D; abaxial including corolla tube nearest RHS 91D.

Gynoecium: Single; tri-carpelled; 52.0 mm long;

*Style.*—Single; cylindrical; arcuate upward about 90° in distal 10 mm; about 44.0 mm long and 1.0 mm diameter; color RHS NN155C.

*Stigma.*—Tri-lobed, micro-puberulent; about 2.0 mm across and 1.0 mm tall; color nearest RHS NN155B.

*Ovary.*—Superior; ellipsoidal; rounded apex and truncate base; lightly longitudinally fluted; about 7.0 mm long and 3.5 mm diameter; color nearest RHS 145B.

Androecium: Six;

*Filaments.*—Cylindrical; glabrous; arcuate upward about 90° in distal 10.0 mm portion; about 50.0 mm long and 0.7 mm diameter; color nearest RHS NN155C.

*Anthers.*—Oblong; dorsifixed, longitudinally dehiscent; about 4.0 mm long and 2.0 mm across and 2.0 mm thick; color variable nearest RHS 200B and RHS 177D.

*Pollen.*—Smaller than 0.1 mm diameter; color nearest RHS 15C.

Flower bud: Clavate; with acute apex and fused tubular base; about 44.0 mm long in total and 9.0 mm wide in bulb portion, tube about 14.0 mm long and 3.5 mm diameter;

Flower bud color: Nearest RHS 91C;

Pedicel: Cylindrical, glabrous, lustrous; outwardly; to about 5.0 mm long and 2.0 mm diameter;

Pedicel color: Nearest blend of RHS 85C and lighter than RHS N77D;

Peduncle: Cylindrical; usually one per mature division and five per plant; slightly glaucous; glabrous; very stiff, rigid; nearly upwardly with slight outwardly angle; to about 82.0 cm long and about 8.0 mm diameter; flowering in upper 16.0 cm with about 28 flowers per scape;

Peduncle color: When flowering nearest blend of RHS 146C and RHS N138B;

Fruit: Tri-valved dehiscent capsule; ellipsoidal to cylindrical with apiculate apex and attenuate base; about 24.0 mm long and 6.0 mm diameter;

Fruit color: Between RHS N138B and RHS 147B;

Seed: Typically about 27 per capsule; endospermic; flattened-ellipsoidal wing surrounding embryo at one end of ellipse; to about 7.0 mm long, 3.0 mm wide and 1.2 mm thick at embryo;

Seed color: Nearest RHS 202A;

Disease tolerance and resistance: The new plant has not shown any resistance to pests, including *Odocoileus virginianus* and *Oryctotagus cuniculus*, and diseases common to *Hostas*. The plant grows best and shows best coloration with plenty of moisture, adequate drainage and light shade, but is able to tolerate some drought when mature. Hardiness at least from USDA zone 3 through 9.

It is claimed:

1. A new and distinct ornamental plant cultivar named *Hosta* 'Hope Springs Eternal' as herein described and illustrated.

* * * * *